(12) United States Patent
Beck et al.

(10) Patent No.: US 6,202,225 B1
(45) Date of Patent: Mar. 20, 2001

(54) FEMALE URINARY DEVICE

(76) Inventors: Gregory A. Beck; Mauritza Beck, both of P.O. Box 380938, Murdock, FL (US) 33938-0938

( * ) Notice: Subject to any disclaimer, the term of this patent is extended or adjusted under 35 U.S.C. 154(b) by 0 days.

(21) Appl. No.: 09/569,627

(22) Filed: May 12, 2000

(51) Int. Cl.[7] .................................................. A47K 11/00
(52) U.S. Cl. ........................... 4/144.2; 4/144.3; 4/144.4; 141/337
(58) Field of Search ................................ 4/144.1–144.4; 141/337, 338, 331

(56) References Cited

U.S. PATENT DOCUMENTS

| | | | |
|---|---|---|---|
| 2,100,888 | * 11/1937 | Vine | 141/337 |
| 5,333,330 | * 8/1994 | Murtagh | 4/144.3 |

* cited by examiner

Primary Examiner—Henry J. Recla
Assistant Examiner—Tuan Nguyen

(57) ABSTRACT

A female urinary device for allowing a female to urinate without splattering and without having to sit upon a toilet. The female urinary device includes a first sheet of material including a main portion having a top edge, a bottom edge, and side edges and being essentially tapered from the top edge to the bottom edge and also having a plurality of pleats spaced apart and extending from the top edge to the bottom edge with the main portion being foldable into a funnel having an open top and an open bottom with the side edges being securely fastenable to one another and with the first sheet of material also having a flap portion being securely attached to the top edge of the main portion; and also includes a second sheet of material having a top edge, a bottom edge, and side edges and also having a plurality of pleats spaced apart and extending from the top edge to the bottom edge with the second sheet of material being foldable into a chute and with the side edges being securely fastenable to one another and with the chute including an open top and an open bottom and being removably connected to the open bottom of the funnel.

12 Claims, 3 Drawing Sheets

FEMALE URINARY DEVICE

BACKGROUND OF THE INVENTION

1. Field of the Invention

The present invention relates to a urinary device and more particularly pertains to a new female urinary device for allowing a female to urinate without splattering and without having to sit upon a toilet.

2. Description of the Prior Art

The use of a urinary device is known in the prior art. More specifically, a urinary device heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,370,637; U.S. Pat. No. 5,333,330; U.S. Pat. No. 4,937,890; U.S. Pat. No. 5,742,948; U.S. Pat. No. 2,100,888; and U.S. Pat. No. Des. 371,601.

While these devices fulfill their respective, particular objectives and requirements, the aforementioned patents do not disclose a new female urinary device. The inventive device includes a first sheet of material including a main portion having a top edge, a bottom edge, and side edges and being essentially tapered from the top edge to the bottom edge and also having a plurality of pleats spaced apart and extending from the top edge to the bottom edge with the main portion being foldable into a funnel having an open top and an open bottom with the side edges being securely fastenable to one another and with the first sheet of material also having a flap portion being securely attached to the top edge of the main portion; and also includes a second sheet of material having a top edge, a bottom edge, and side edges and also having a plurality of pleats spaced apart and extending from the top edge to the bottom edge with the second sheet of material being foldable into a chute and with the side edges being securely fastenable to one another and with the chute including an open top and an open bottom and being removably connected to the open bottom of the funnel.

In these respects, the female urinary device according to the present invention substantially departs from the conventional concepts and designs of the prior art, and in so doing provides an apparatus primarily developed for the purpose of allowing a female to urinate without splattering and without having to sit upon a toilet.

SUMMARY OF THE INVENTION

In view of the foregoing disadvantages inherent in the known types of urinary device now present in the prior art, the present invention provides a new female urinary device construction wherein the same can be utilized for allowing a female to urinate without splattering and without having to sit upon a toilet.

The general purpose of the present invention, which will be described subsequently in greater detail, is to provide a new female urinary device which has many of the advantages of the urinary device mentioned heretofore and many novel features that result in a new female urinary device which is not anticipated, rendered obvious, suggested, or even implied by any of the prior art urinary device, either alone or in any combination thereof.

To attain this, the present invention generally comprises a first sheet of material including a main portion having a top edge, a bottom edge, and side edges and being essentially tapered from the top edge to the bottom edge and also having a plurality of pleats spaced apart and extending from the top edge to the bottom edge with the main portion being foldable into a funnel having an open top and an open bottom with the side edges being securely fastenable to one another and with the first sheet of material also having a flap portion being securely attached to the top edge of the main portion; and also includes a second sheet of material having a top edge, a bottom edge, and side edges and also having a plurality of pleats spaced apart and extending from the top edge to the bottom edge with the second sheet of material being foldable into a chute and with the side edges being securely fastenable to one another and with the chute including an open top and an open bottom and being removably connected to the open bottom of the funnel.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new female urinary device which has many of the advantages of the urinary device mentioned heretofore and many novel features that result in a new female urinary device which is not anticipated, rendered obvious, suggested, or even implied by any of the prior art urinary device, either alone or in any combination thereof.

It is another object of the present invention to provide a new female urinary device which may be easily and efficiently manufactured and marketed.

It is a further object of the present invention to provide a new female urinary device which is of a durable and reliable construction.

An even further object of the present invention is to provide a new female urinary device which is susceptible of a low cost of manufacture with regard to both materials and labor, and which accordingly is then susceptible of low prices of sale to the consuming public, thereby making such female urinary device economically available to the buying public.

Still yet another object of the present invention is to provide a new female urinary device which provides in the apparatuses and methods of the prior art some of the advantages thereof, while simultaneously overcoming some of the disadvantages normally associated therewith.

Still another object of the present invention is to provide a new female urinary device for allowing a female to urinate without splattering and without having to sit upon a toilet.

Yet another object of the present invention is to provide a new female urinary device which includes a first sheet of material including a main portion having a top edge, a bottom edge, and side edges and being essentially tapered from the top edge to the bottom edge and also having a plurality of pleats spaced apart and extending from the top edge to the bottom edge with the main portion being foldable into a funnel having an open top and an open bottom with the side edges being securely fastenable to one another and with the first sheet of material also having a flap portion being securely attached to the top edge of the main portion; and also includes a second sheet of material having a top edge, a bottom edge, and side edges and also having a plurality of pleats spaced apart and extending from the top edge to the bottom edge with the second sheet of material being foldable into a chute and with the side edges being securely fastenable to one another and with the chute including an open top and an open bottom and being removably connected to the open bottom of the funnel.

Still yet another object of the present invention is to provide a new female urinary device that allows the female to urinate without having to sit upon a toilet seat which may be unsanitary.

Even still another object of the present invention is to provide a new female urinary device that can be easily stored and taken with the person and then easily disposed after usage.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
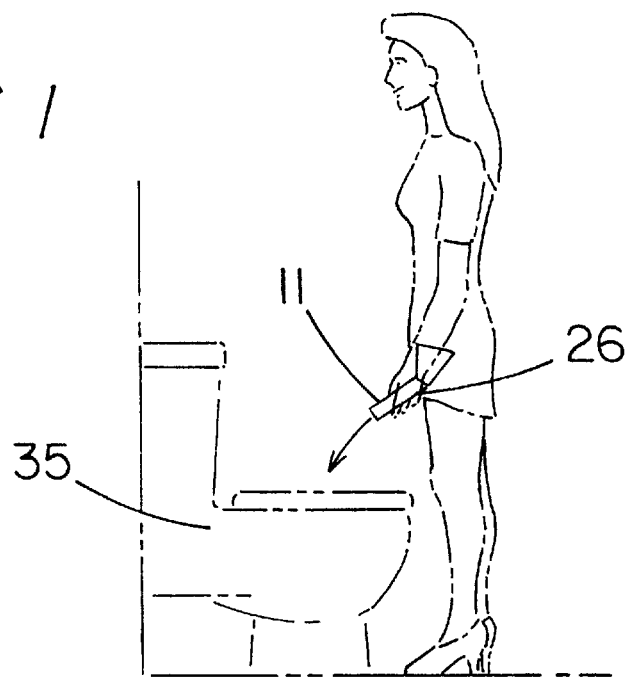
FIG. 1 is a side elevational view of a new female urinary device according to the present invention shown in use.
Figure 2:
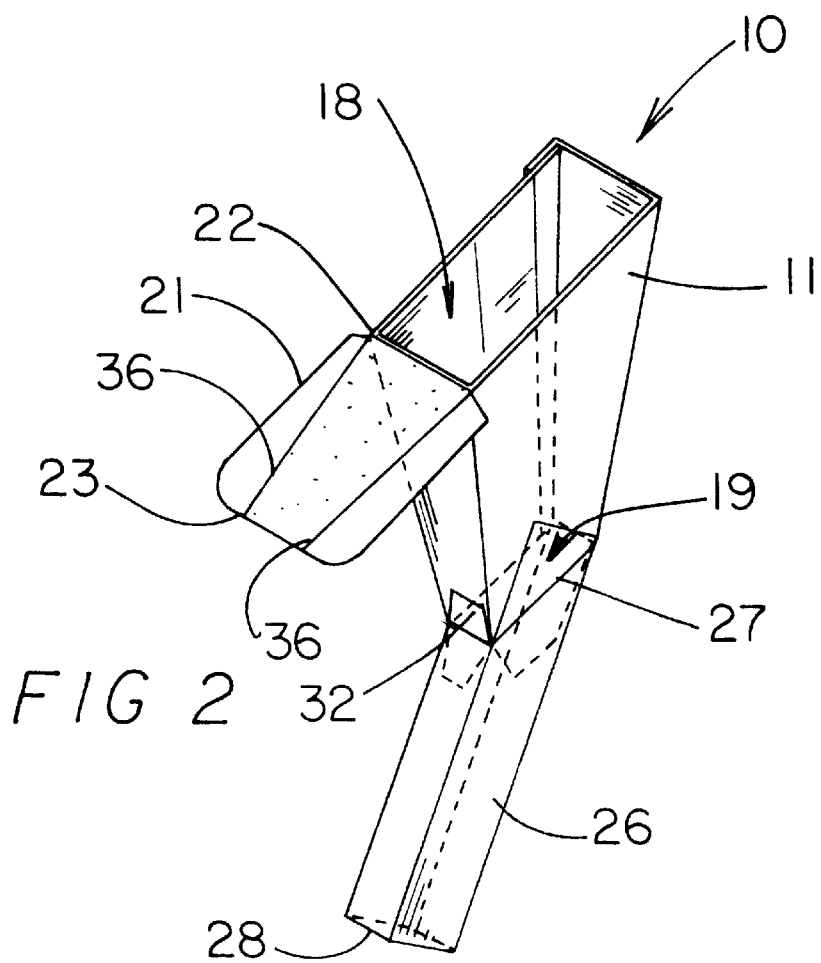
FIG. 2 is a perspective view of the present invention.
Figure 3:
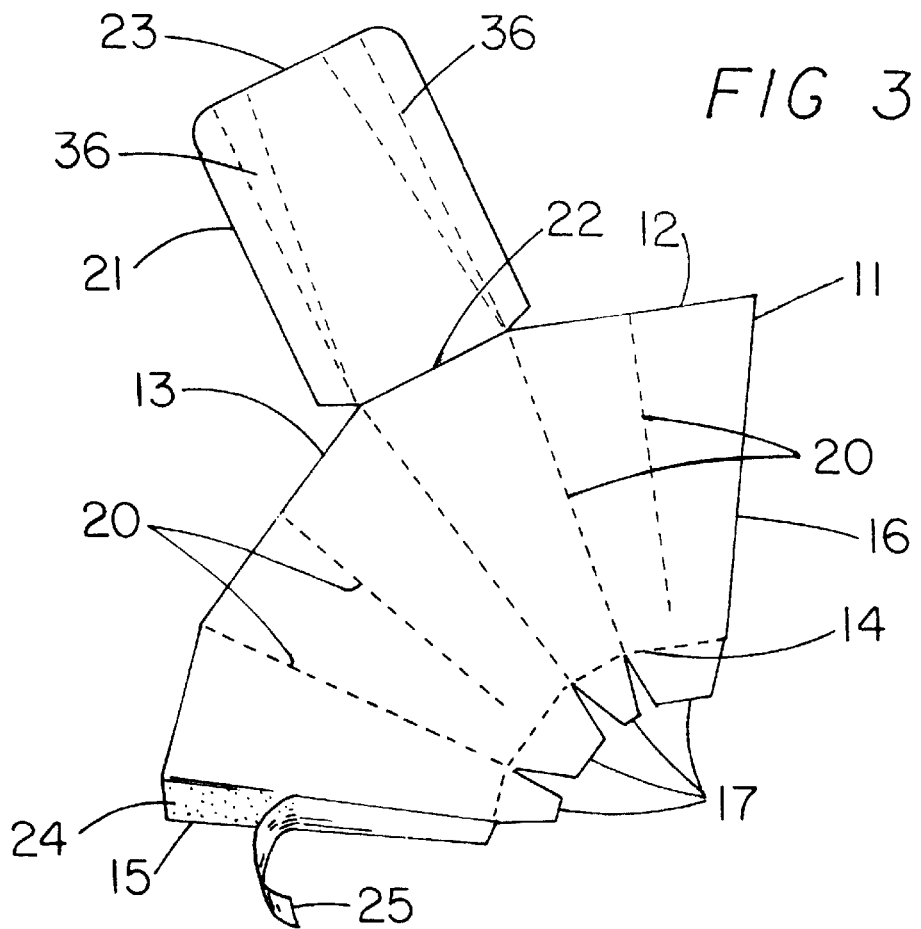
FIG. 3 is a perspective view of the first sheet of material of the present invention.
Figure 4:
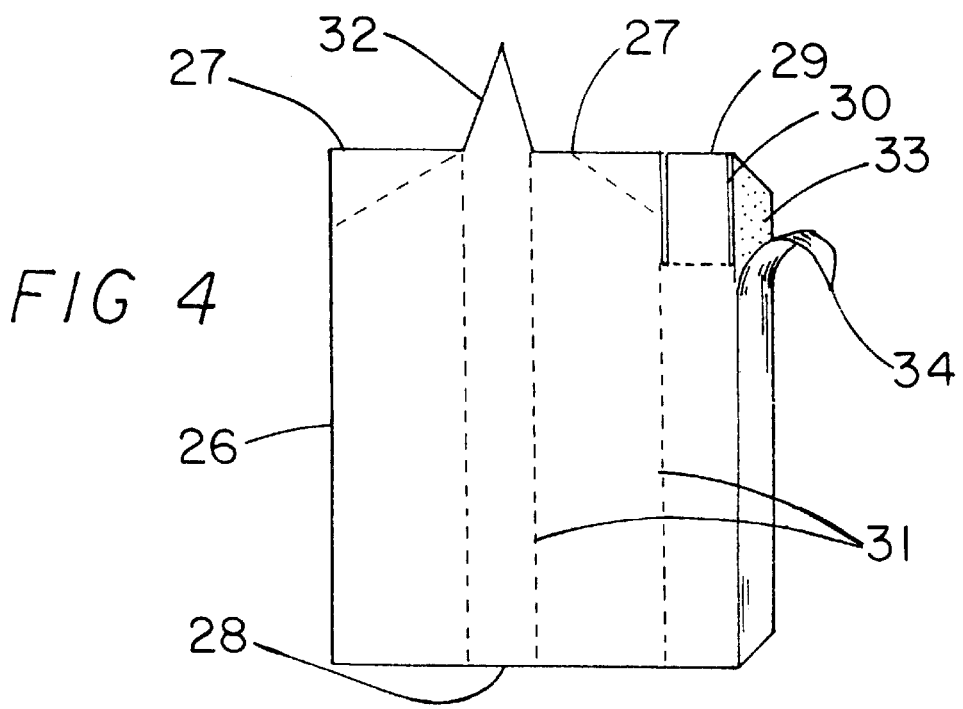
FIG. 4 is a perspective view of the second sheet of the present invention.
Figure 5:
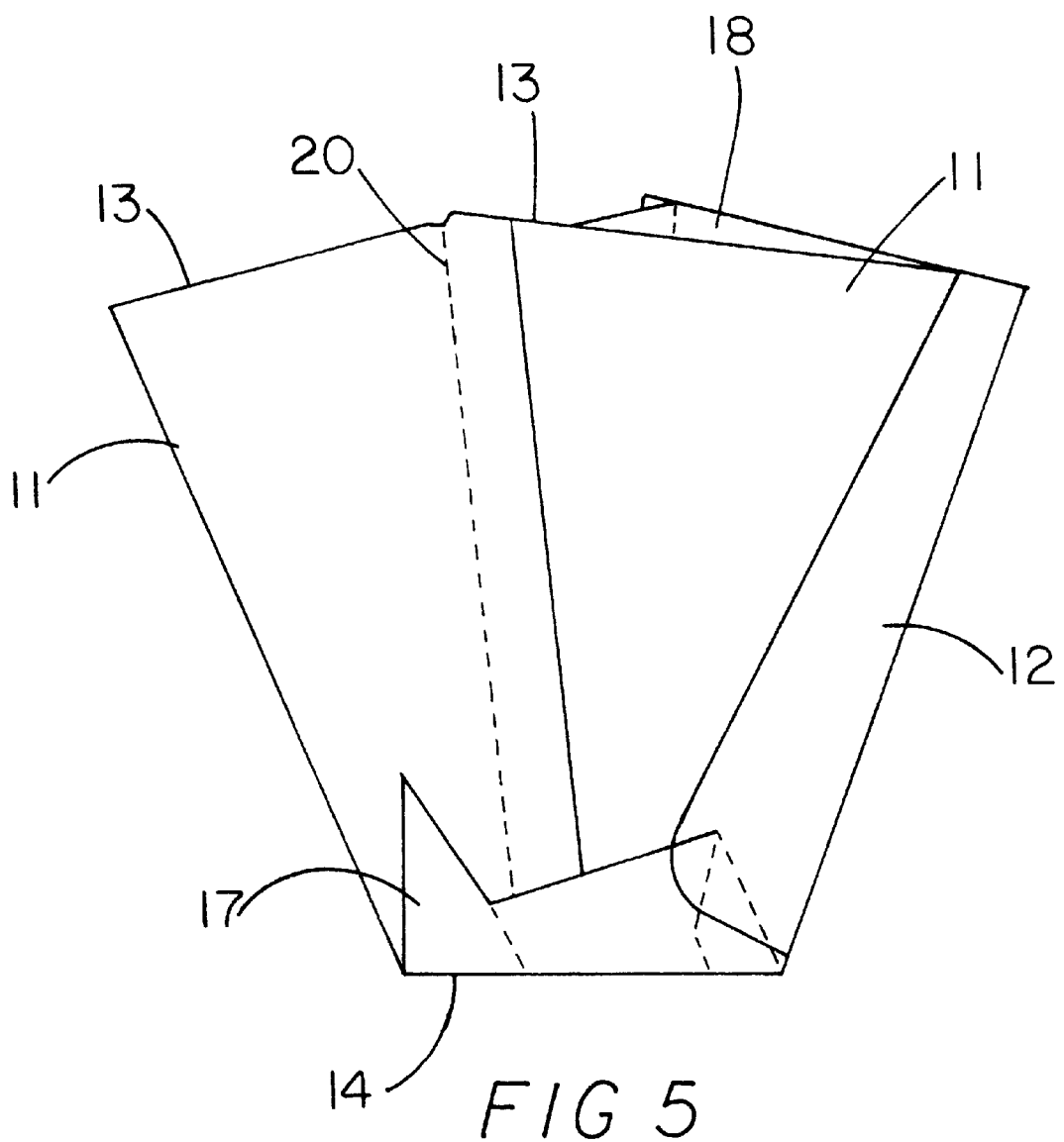
FIG. 5 is a perspective view of the first sheet of material of the present invention.

With reference now to the drawings, and in particular to FIGS. 1 through 5 thereof, a new female urinary device embodying the principles and concepts of the present invention and generally designated by the reference numeral 10 will be described.

As best illustrated in FIGS. 1 through 5, the female urinary device 10 generally comprises a first sheet of material 11 including a main portion 12 having a top edge 13, a bottom edge 14, and side edges 15,16 and being essentially tapered from the top edge 13 to the bottom edge 14 and also having a plurality of pleats 20 spaced apart and extending from the top edge 13 to the bottom edge 14. The main portion 12 is foldable into a funnel having an open top 18 and an open bottom 19 with the side edges 15,16 being securely fastenable to one another. The first sheet of material 11 also has a flap portion 21 being securely and integrally attached to the top edge 13 of the main portion 12. The flap portion 21 includes a proximate edge 22 which is securely attached to a portion of the top edge 13 of the first sheet of material 11 and also includes a distal edge 23. The flap portion 21 further includes a plurality of pleats 36 extending from the proximate edge 22 to the distal edge 23. The first sheet of material 11 includes a strip of adhesive 24 extending along one of the side edges thereof and being adherable to the other of the side edges 15 of the first sheet of material 11 to form the funnel. The first sheet of material 11 includes a strip of material 25 being removably disposed upon the strip of adhesive 24 for the protection thereof. The flap portion 21 is essentially made of absorbent material for use as a wipe.

A second sheet of material 26 having a top edge 27, a bottom edge 28, and side edges 29,30 and also having a plurality of pleats 31 spaced apart and extending from the top edge 27 to the bottom edge 28 with the second sheet of material 26 being foldable into a chute with the side edges 29,30 being securely fastenable to one another. The chute includes an open top and an open bottom and is removably connected to the open bottom 19 of the funnel. Also, the first sheet of material 11 includes a plurality of bendable tab members 17 integrally attached along and extending from the bottom edge 14 thereof with the tab members 17 being extendable into the open top of the chute to essentially engage side walls of the chute and to facilitate connecting of the chute to the funnel. The second sheet of material 26 includes at least one tab member 32 extending from a portion of the top edge 27 thereof and being extendable in the open bottom 19 of the funnel and being engageable with at least one side wall of the funnel to securely retain the chute to the funnel. The second sheet of material 26 includes a strip of adhesive 33 extending along one of the side edges 30 thereof and being adherable to the other of the side edges 29 of the second sheet of material 26 to form the chute. The second sheet of material 26 includes a strip of material 34 being removably disposed upon the strip of adhesive 33 with the chute being angled relative to the funnel to effectively direct urine into a toilet 35. The chute and the flap portion 21 essentially extend in a same direction. The first and second sheets of material 11,26 are essentially made of paper.

In use, the user would place the open top 18 of the funnel about the urethra and direct the angled chute into the toilet 35 and would urinate into the toilet 35 without the female having to sit upon the toilet. Once finished, the user can simply throw the disposable female urinary device 10 away.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A disposable female urinary device comprising:
a first sheet of material including a main portion having a top edge, a bottom edge, and side edges and being essentially tapered from said top edge to said bottom edge and also having a plurality of pleats spaced apart and extending from said top edge to said bottom edge, said main portion being foldable into a funnel having an open top and an open bottom with said side edges being securely fastenable to one another, said first sheet of material also having a flap portion being securely attached to said top edge of said main portion; and
a second sheet of material having a top edge, a bottom edge, and side edges and also having a plurality of pleats spaced apart and extending from said top edge to said bottom edge, said second sheet of material being foldable into a chute with said side edges being securely fastenable to one another, said chute including an open top and an open bottom and being removably connected to said open bottom of said funnel.

2. A disposable female urinary device as described in claim 1, wherein said first sheet of material includes a plurality of bendable tab members attached along and extending from said bottom edge thereof, said tab members being extendable into said open top of said chute to essentially engage side walls of said chute and to facilitate connecting of said chute to said funnel.

3. A disposable female urinary device as described in claim 2, wherein said flap portion includes a proximate edge which is securely attached to a portion of said top edge of said first sheet of material, and also includes a distal edge, said flap portion further includes a plurality of pleats extending from said proximate edge to said distal edge.

4. A disposable female urinary device as described in claim 3, wherein said first sheet of material includes a strip of adhesive extending along one of said side edges thereof and being adherable to the other of said side edges of said first sheet of material.

5. A disposable female urinary device as described in claim 4, wherein said first sheet of material includes a strip of material being removably disposed upon said strip of adhesive.

6. A disposable female urinary device as described in claim 5, wherein said second sheet of material includes at least one tab member extending from a portion of said top edge thereof and being extendable in said open bottom of said funnel and being engageable with at least one side wall of said funnel to securely retain said chute to said funnel.

7. A disposable female urinary device as described in claim 6, wherein said second sheet of material includes a strip of adhesive extending along one of said side edges thereof and being adherable to the other of said side edges of said second sheet of material.

8. A disposable female urinary device as described in claim 7, wherein said second sheet of material includes a strip of material being removably disposed upon said strip of adhesive.

9. A disposable female urinary device as described in claim 8, wherein said chute is angled relative to said funnel to effectively direct urine into a toilet, said chute and said flap portion essentially extending in a same direction.

10. A disposable female urinary device as described in claim 9, wherein said first and second sheets of material are essentially made of paper.

11. A disposable female urinary device as described in claim 10, wherein said flap portion is essentially made of absorbent material for use as a wipe.

12. A disposable female urinary device comprising:
a first sheet of material including a main portion having a top edge, a bottom edge, and side edges and being essentially tapered from said top edge to said bottom edge and also having a plurality of pleats spaced apart and extending from said top edge to said bottom edge, said main portion being foldable into a funnel having an open top and an open bottom with said side edges being securely fastenable to one another, said first sheet of material also having a flap portion being securely attached to said top edge of said main portion, said first sheet of material including a plurality of bendable tab members attached along and extending from said bottom edge thereof, said flap portion including a proximate edge which is securely attached to a portion of said top edge of said first sheet of material, and also including a distal edge, said flap portion further including a plurality of pleats extending from said proximate edge to said distal edge, said first sheet of material including a strip of adhesive extending along one of said side edges thereof and being adherable to the other of said side edges of said first sheet of material to form said funnel, said first sheet of material including a strip of material being removably disposed upon said strip of adhesive, said flap portion being essentially made of absorbent material for use as a wipe; and
a second sheet of material having a top edge, a bottom edge, and side edges and also having a plurality of pleats spaced apart and extending from said top edge to said bottom edge, said second sheet of material being foldable into a chute with said side edges being securely fastenable to one another, said tab members of said first sheet of material being extendable into said open top of said chute to essentially engage side walls of said chute and to facilitate connecting of said chute to said funnel, said chute including an open top and an open bottom and being removably connected to said open bottom of said funnel, said second sheet of material including at least one tab member extending from a portion of said top edge thereof and being extendable in said open bottom of said funnel and being engageable with at least one side wall of said funnel to securely retain said chute to said funnel, said second sheet of material including a strip of adhesive extending along one of said side edges thereof and being adherable to the other of said side edges of said second sheet of material to form said chute, said second sheet of material including a strip of material being removably disposed upon said strip of adhesive, said chute being angled relative to said funnel to effectively direct urine into a toilet, said chute and said flap portion essentially extending in a same direction, said first and second sheets of material being essentially made of paper.

* * * * *